United States Patent
Seale et al.

(10) Patent No.: US 11,690,576 B2
(45) Date of Patent: *Jul. 4, 2023

(54) APPARATUS AND METHODS FOR DETECTING CARDIAC ARREST

(71) Applicant: Health Alert, LLC, Angwin, CA (US)

(72) Inventors: Walter L. Seale, Boise, ID (US); Alois A. Langer, Harrison City, PA (US); Nicholas J. Pauly, Boise, ID (US); Mark Francis Anderson, Boise, ID (US)

(73) Assignee: Health Alert, LLC, Angwin, CA (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/208,675

(22) Filed: Mar. 22, 2021

(65) Prior Publication Data

US 2021/0290182 A1 Sep. 23, 2021

Related U.S. Application Data

(63) Continuation of application No. 15/801,186, filed on Nov. 1, 2017, now Pat. No. 10,952,685.

(51) Int. Cl.
*A61B 5/07* (2006.01)
*A61B 5/00* (2006.01)
*A61B 5/024* (2006.01)
*A61B 5/11* (2006.01)
*A61B 5/01* (2006.01)

(52) U.S. Cl.
CPC .............. *A61B 5/7282* (2013.01); *A61B 5/01* (2013.01); *A61B 5/02416* (2013.01); *A61B 5/11* (2013.01); *A61B 5/746* (2013.01); *A61B 2560/0209* (2013.01); *A61B 2562/0219* (2013.01)

(58) Field of Classification Search
CPC .......................... A61B 5/02416; A61B 5/7282
See application file for complete search history.

(56) References Cited

U.S. PATENT DOCUMENTS

| | | | |
|---|---|---|---|
| 10,952,685 B2* | 3/2021 | Seale | ..................... A61B 5/746 |
| 2013/0172703 A1 | 7/2013 | Dixon et al. | |
| 2017/0172424 A1 | 6/2017 | Eggers et al. | |
| 2019/0125276 A1 | 5/2019 | Seale et al. | |

OTHER PUBLICATIONS

Seale, et al., Notice of Allowance dated Nov. 17, 1010 for U.S. Appl. No. 15/801,186.
Seale, et al., Office Action dated Mar. 31, 2020 for U.S. Appl. No. 15/801,186.

* cited by examiner

Primary Examiner — Alyssa M Alter
(74) Attorney, Agent, or Firm — Stoel Rives LLP

(57) ABSTRACT

Apparatus and methods for detecting onset of cardiac arrest utilizing a perfusion monitor. Detecting cardiac arrest comprises transmitting a signal toward a user to interact with the skin of the user, receiving a reflection of the signal, generating a photoplethysmogram, and processing the photoplethysmogram to detect whether the user is experiencing cardiac arrest.

20 Claims, 8 Drawing Sheets

APPARATUS AND METHODS FOR DETECTING CARDIAC ARREST

RELATED APPLICATIONS

This application is a continuation of U.S. patent application Ser. No. 15/801,186 filed Nov. 1, 2017, issued as U.S. Pat. No. 10,952,685 on Mar. 23, 2021, and titled APPARATUS AND METHODS FOR DETECTING CARDIAC ARREST, the entirety of which is incorporated herein by reference.

TECHNICAL FIELD

The present disclosure relates to detecting onset of a change in a health condition, and more particularly to apparatus and methods for detecting onset of cardiac arrest.

BACKGROUND

Cardiac arrest may occur in more than 300,000 Americans each year. If a witness is present when a person falls victim, the chances of survival are greatly increased. Unfortunately, nearly one half of cardiac arrest events occur with no witness present. In such cases as this, the chances of survival are minimal. A common occurrence is a victim who dies in his sleep, or one who collapses at home merely feet from a potential rescuer who is in another room, unaware of the collapse.

Although the survival rate for witnessed events is also relatively low, there are procedures available and tools that could be used by laypersons that could potentially increase the chances of survival for any individual case. For example, many victims may be promptly resuscitated with placement of an external defibrillator, or by application of proven medical strategies such as therapeutic hypothermia and immediate heart catheterization. In any case, the chances for survival depend heavily on the notification of potential rescuers.

High-risk groups also have a relatively small chance of falling victim to cardiac arrest, and individuals that do not belong to such groups may have an even smaller probability of falling victim to cardiac arrest than the high-risk groups. To detect the relatively few unfortunate victims, a substantial number of people may be monitored.

Monitoring many individuals on a continuous basis represents a challenging technological endeavor. Traditional monitoring techniques rely on electrocardiographic (ECG) recordings. These recordings require highly technical recorders and analysis techniques, are prone to noise that mimics life-threatening heart rhythm disturbance, and are inappropriate for continuous daily use. Additionally, even a theoretically perfect continuous ECG recording device would likely be prohibitively expensive for use on populations. Lastly, it would be unable to discern Pulseless Electrical Activity (PEA)—cardiac arrest that occurs with preservation of ECG signals.

Accordingly, other techniques, apparatus, and methods to monitor for cardiac arrest may be desirable.

SUMMARY

The present disclosure is directed to apparatus and methods for detecting onset of cardiac arrest. The disclosed embodiments detect perfusion, or a lack thereof, by obtaining photoplethysmogram data and interpreting the data.

BRIEF DESCRIPTION OF THE DRAWINGS

Additional aspects and advantages will be apparent from the following detailed description of preferred embodiments, which proceeds with reference to the accompanying drawings, in which.

DETAILED DESCRIPTION

Cardiac arrest is a sudden stop in effective blood flow due to a failure of the heart to contract effectively. If not treated within minutes, death of the victim is highly likely. When no witness is present, timely medical treatment is unlikely, and the survival rate is low (e.g., essentially zero). If a witness is present when a person falls victim to cardiac arrest, the chances of survival are greatly increased, because of the possibility of timely medical treatment. Monitoring could potentially be adequate to replace a witness to an event of cardiac arrest and to improve chances of survival of the victim.

Monitoring many individuals on a continuous basis, however, represents a challenging technological endeavor. Traditional monitoring techniques rely on electrocardiographic (ECG) recordings. These recordings require highly technical recorders and analysis techniques, are prone to noise that mimics life-threatening heart rhythm disturbances, and are inappropriate for continuous daily use. Additionally, even a theoretically perfect continuous ECG recording device would likely be prohibitively expensive for use on populations.

Newer, commercially available, externally worn heart rate monitors rely on optically derived photoplethysmography. Photoplethysmography is an optical technique that involves obtaining and interpreting photoplethysmogram (PPG) data. The PPG data contains information from which a physiological signal may be derived. In some examples, PPG data can be graphed to show plotted values that correspond to the magnitude of an optical signal. Photoplethysmographic devices utilize signals (and thereby generate PPGs) that are susceptible to motion-artifact and, as such, heart rate measurements reported by these devices are notoriously inaccurate. Nevertheless, accurate detection of cardiac arrest can be accomplished by certain analyses of PPG data. Herein are disclosed apparatus and methods for analyzing PPG data to detect cardiac arrest. Convenient and relatively inexpensive monitoring of large numbers of persons can be accomplished on a continuous basis given that sensors can be configured to be worn in everyday devices such as a wristwatch.

The present disclosure will be better understood from the detailed description provided below and from the drawings of various embodiments, methods, and examples herein. These specifics, however, are provided for explanatory purposes that help the various embodiments of the disclosure to be better understood. The embodiments described herein should therefore not be limited by the described methods and examples.

Figure 1:
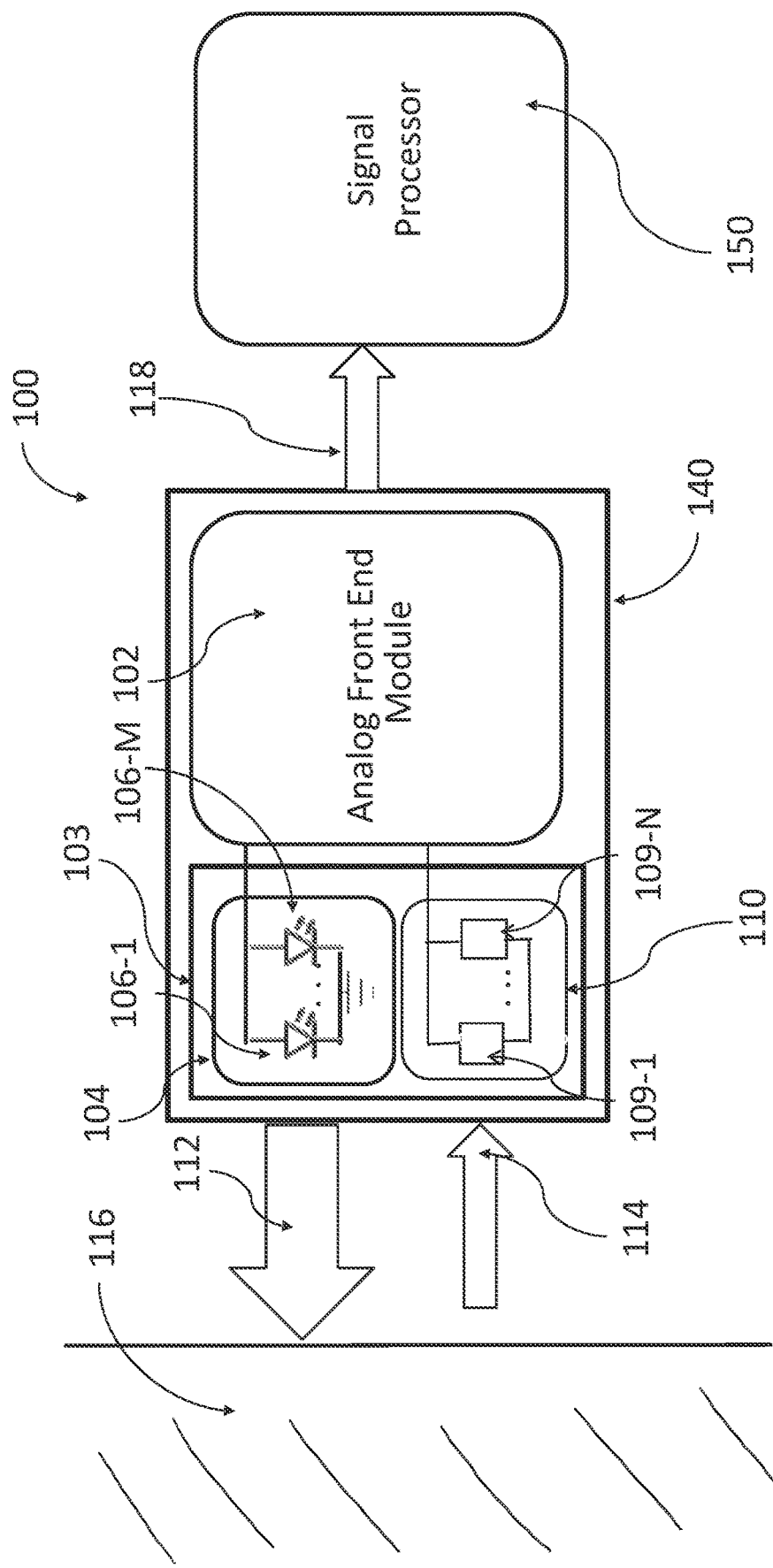
FIG. 1 is a block diagram of a perfusion detector for detecting cardiac arrest, according to one embodiment.

FIG. 1 is a block diagram of a perfusion detector for detecting cardiac arrest, according to one embodiment. The perfusion detector 100 may include a photoplethysmographic measuring device 140 and a signal processor 150. The perfusion detector 100 may optically obtain and/or generate PPG data (e.g., referred to herein as PPG) of a user (e.g., wearer) of the perfusion detector 100 to monitor for a loss of a pulsatile pattern. The PPG may be processed to detect potential cardiac arrest in the user.

The photoplethysmographic measuring device 140 may include a sensor module 103, and an analog front-end module (AFE) 102. The sensor module 103 may comprise a transmitter module 104 and a receiver module 110. An output signal 118 may be sent from the photoplethysmographic measuring device 140 to the signal processor 150, where the output signal 118 (e.g., including data of an optically obtained PPG) can be processed to determine whether perfusion (or lack thereof) may indicate potential cardiac arrest.

In various embodiments, the photoplethysmographic measuring device 140 may transmit an electromagnetic signal 112 from the transmitter module 104 by means of one or more of the individual signal sources 106-1 to 106-M, with the intent that the electromagnetic signal 112 interacts with a user's skin 116. As used herein, the individual signal sources 106-1 to 106-M are referred to as individual signal sources 106. The electromagnetic signal 112 may have sufficient strength to penetrate the user's skin 116 to a certain depth and interact with the user's blood cells. Some of the electromagnetic signal 112 may reflect at a rate proportional to an amount (e.g., volume) of blood cells flowing through a particular conduit(s) within the path of the electromagnetic signal 112. The reflected input signal 114 can be received by one or more individual transducers (e.g., individual transducers 109-1 to 109-N) of the receiver module 110. The reflected input signal 114 is then converted into an electrical signal. As used herein, the individual transducers 109-1 to 109-N can be referred to as individual transducers 109 and may denote one or more individual transducers. Stated otherwise, a PPG is at least partially generated from a reflection of the electromagnetic signal 112.

In various embodiments, the electromagnetic signal 112 may be red, green, or blue light, or any combination thereof. The signal sources 106 may be light sources. In some embodiments, the electromagnetic signal 112 may have a fundamental frequency that is not within the spectrum of visible light. The fundamental frequency can be infrared or ultraviolet light, but is not limited to such. In other embodiments, the electromagnetic signal 112 may be replaced by or used in conjunction with an audio signal. In some embodiments, the individual signal sources 106 may be light sources. For example, the individual signal sources 106 may be light emitting diodes (LEDs) that emit green light, and the individual transducers 109 may be photodiodes.

In some embodiments, the transmitter module 104 may utilize multiple of the individual signal sources 106 to vary a resolution of the reading, as well as to vary power consumption. For example, the perfusion detector 100 may by default illuminate one of the individual signal sources 106 and if there appears to be a poor reading and/or low resolution of the reflected input signal 114, other of the individual signal sources 106 may be illuminated before a presence or loss of perfusion is determined. If a sufficiently strong reading or high resolution of the reflected input signal 114 is achieved, the auxiliary signal sources may be turned off to return to the default power consumption.

In some embodiments, the transmitter module 104 may be an array of the individual signal sources 106, where each of the individual signal sources 106 is positioned adjacent to the next. In other embodiments, the individual signal sources 106 in the transmitter module 104 may be angled and/or positioned advantageously to guide the reflected input signal 114 directly toward the receiver module 110. In some embodiments, the material in which the individual signal sources 106 are embedded may be shaped and/or coated around the individual signal sources 106. Shaping and/or coating material around the individual signal sources 106 may allow the electromagnetic signal 112 to be transmitted more effectively toward the target area. In some embodiments, the individual signal sources 106 may be light emitting diodes, organic light emitting diodes, light emitting electrochemical cells, and/or the like.

The receiver module 110 uses the individual transducers 109 to convert the reflected input signal 114 from the user's skin 116 into an electrical signal that can be amplified, filtered, and/or processed. Various embodiments may incorporate more than one of the individual transducer 109 in the receiver module to increase a resolution or reading of the reflected input signal 114 and/or to vary power consumption. For example, the perfusion detector 100 may, by default, provide power to and read from one individual transducer (e.g., the individual transducer 109-1) in the receiver module 110, and if there is a poor reading or low resolution of the reflected input signal 114, other individual transducers (e.g., the individual transducer 109-N) may be powered and read from before a loss or presence of perfusion is determined. If a sufficiently strong reading or high resolution of the reflected input signal 114 is achieved, the perfusion detector 100 may stop the flow of power to all but one or a few of the individual transducers 109 to return to the default power consumption.

In some embodiments, the transmitter module 104 includes multiple of the individual signal sources 106 as well as the individual transducers 109. The perfusion detector 100 may then vary a resolution of the reading of the reflected input signal 114 to be more precise by varying the number of illuminated individual signal sources 106 in the transmitter module 104 and/or powered individual transducers 109 in the receiver module 110. The best reading of the reflected input signal 114 may be achieved when the maximum number of individual signal sources 106 in the transmitter module 104 are illuminated and the maximum number of individual transducers 109 in the receiver module 110 are powered simultaneously. Power consumption may vary between the transmitter module 104 and receiver module 110. In some examples, the receiver module 110 may be utilized more heavily than the transmitter module 104. For example, depending on the devices chosen as the individual transducers 109 in the receiver module 110 and individual signal sources 106 in the transmitter module 104, it may be more favorable to illuminate one of the individual signal sources 106 in the transmitter module 104 and power several of the individual transducers 109 in the receiver module 110.

In some embodiments, the individual transducers 109 in the receiver module 110 may be positioned such that they are adjacent to each other. In some embodiments, the individual transducers 109 in the receiver module 110 may be angled and/or positioned advantageously such that the reflected input signal 114 is received more directly. The transmitter module 104 and receiver module 110 may be integrated in such a way that the individual signal sources 106 are located on either side of one or more of the individual transducers 109. In certain embodiments, the individual transducers 109 may be surrounded by the individual signal sources 106. In some embodiments, the material in which the individual transducers 109 are embedded may be shaped and/or coated in such a way that the reflected input signal 114 may be more effectively directed towards the individual transducers 109. In some embodiments, the individual transducers 109 may be coated with a substance that filters unwanted frequencies from the reflected input signal 114. The individual transducers 109 may be photodiodes, phototransistors, photoresistors, and/or the like.

The AFE 102 may serve as an interface for the transmitter module 104 and the receiver module 110. The AFE 102 may include the power supplies for the transmitter module 104 and the receiver module 110 respectively. If the perfusion detector 100 requires that the electromagnetic signal 112 be pulsed, the AFE 102 may comprise a clock or counter. The AFE 102 may comprise a control structure such as an LED driver for switching on and off various individual portions of the transmitter and/or receiver modules 104, 110 respectively (such as the individual signal sources 106 and/or the individual transducers 109). If the perfusion detector 100 requires that the amplitude of the electromagnetic signal 112 be varied, the AFE 102 may comprise amplifying and/or attenuating circuitry. If the perfusion detector 100 requires that the resolution of the reflected input signal 114 be varied, the AFE 102 may comprise the appropriate amplifying and/or attenuating circuitry.

The photoplethysmographic measuring device 140 may produce the output signal 118 that may be passed to a signal processor 150. The signal processor 150 may then analyze the data from the output signal 118 and make a determination of whether perfusion is present, thereby detecting potential cardiac arrest.

The signal processor 150 may comprise one or more general purpose microcontrollers and/or microprocessors. The signal processor 150 may receive the output signal 118 from the photoplethysmographic measuring device 140, configure the data from the output signal 118 into a PPG, make a physiological determination, and transmit information regarding the determination (such as a personal alarm or initiation of an alarm cascade) to a variety of external receivers. In some embodiments, the information may be a personal alarm or initiation of an alarm cascade. In other embodiments, the information may be data for a PPG. In some applications, the external receiver may be a cell phone(s) of the user's personally selected emergency contact(s) or caregiver(s). In some applications, the external receiver may be door locks to the user's home, external defibrillators, and/or an audible alarm. In some applications, the external receiver may include a display unit such as a computer monitor or wristwatch display screen whereby a PPG may be viewed.

In some examples, the personal alarm or the alarm cascade can be implemented utilizing an alarm mechanism (not shown) to alert others that the user is experiencing cardiac arrest. The alarm mechanism can be initiated based on a determination that the user is experiencing cardiac arrest. The alarm mechanism can also, upon detection of cardiac arrest in the user, attempt to arouse a response in the user. The alarm may include location information to indicate to a receiver of the alarm the whereabouts or location of the user.

Figure 2:
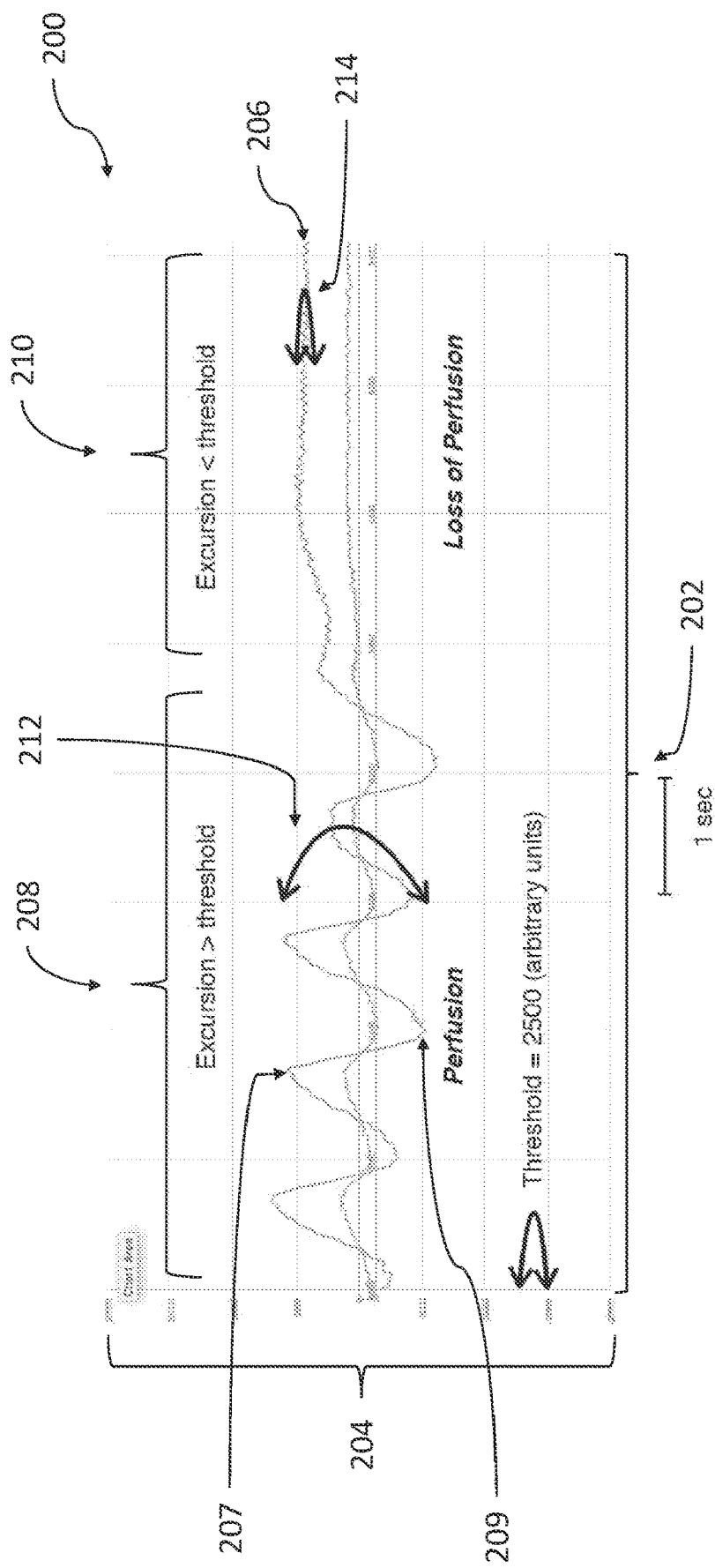
FIG. 2 is a graph illustrating an example of a photoplethysmogram captured by a photoplethysmographic measuring device, according to one embodiment.

FIG. 2 is a graph 200 illustrating an example of a PPG 206 (e.g., PPG data representing a physiological characteristic or measurement) captured by a photoplethysmographic measuring device 140, according to one embodiment. The PPG 206 of FIG. 2 illustrates where perfusion is present 208 transitioning to loss of perfusion 210, demonstrating how a loss of perfusion 210 may be detected.

In the graph 200 of FIG. 2, the horizontal axis 202 represents units of time and the vertical axis 204 represents an arbitrary signal level. The graph 200 illustrates the values that the PPG 206 may take on when perfusion is present 208 and when there is a loss of perfusion 210. The PPG 206 is proportional to a reflected input signal from the user's blood cells. When perfusion is present 208 and the cardiac cycle is at a maximum (e.g., during cardiac systole, when the heart is contracting and the capillary-level blood vessels expand), the blood volume within the conduit(s) of focus will increase. Consequently, during this cardiac cycle, a reflected input signal may increase and the PPG 206 may reach a local maximum value 207. When perfusion is present 208 and the cycle is at a minimum (e.g., during cardiac diastole, when the heart is filling), the blood volume within the conduit(s) of focus will decrease. Consequently, during this cardiac cycle, the reflected input signal may decrease and the PPG 206 may reach a local minimum value 209.

When perfusion is present 208, the difference 212 between the maximum value 207 and the minimum value 209 of a cycle of the PPG 206 may be relatively large. In some examples, the difference 212 may be measured during a time sample encompassing one or more cycles. A time sample may comprise two seconds, 10 seconds, or a different duration of time that includes multiple cycles of heart action. A maximum of one cycle may be compared to a minimum of a different cycle to compute the difference 212 and/or an excursion.

When there is a loss of perfusion 210, the difference 214 between a maximum value 207 and a minimum value 209 of a cycle of the PPG 206 may be relatively small as compared to the difference 212. In some examples, the excursion of the maximum value 207 and the minimum value 209 associated with the difference 212, and a maximum value and a minimum value associated with the difference 214 of a cycle of the PPG 206, can be assessed to determine whether perfusion is present 208.

Excursion is defined as the difference between the maximum value 207 and the minimum value 209 of the PPG 206. Equation 1 can be used to calculate the signal excursion:

$$E = A_{max} - A_{min} \qquad \text{Equation 1}$$

In equation 1 above, E is the signal excursion, $A_{max}$ is a maximum value (e.g., the maximum value 207) of the PPG 206, and $A_{min}$ is a minimum value (e.g., the minimum value 209) of the PPG 206 within a given time period, such as one or more cycles (e.g., two seconds, ten seconds, or a different duration of time).

For each new data point, the new data point (e.g., the physiological signal value) may be compared to the most recently stored maximum value 207 and minimum value 209, and then the new data point can replace either the maximum value 207 or the minimum value 209 if the new data point exceeds the maximum value 207 or falls below the minimum value 209. A specified time period may be selected in which the PPG 206 data may be stored. The maximum value 207 or the minimum value 209 that is older than a predetermined time period may be discarded and replaced with a new maximum value and/or a new minimum value.

The process for determining whether perfusion is present 208 may include establishing an alert threshold. The alert threshold is a minimum excursion value below which perfusion is assumed to be absent. The alert threshold may be calculated using equation 2 below:

$$Th = m_p E_{median} \qquad \text{Equation 2}$$

In equation 2, Th is the alert threshold, $m_p$ is a threshold percentage, and $E_{median}$ is the median of excursion values established at a baseline recording.

The threshold percentage $m_p$ may be selected such that the alert threshold Th is a smaller value than the excursion value when perfusion is present 208. For example, the threshold percentage $m_p$ may be equal to 10%, such that if the detected excursion is below 10% of the median excursion $E_{median}$ the alert threshold is broken.

The baseline recording for obtaining the median excursion $E_{median}$ may occur at a time appropriate for establishing a reliable median. For example, the baseline recording may occur one day prior to the current period of analysis.

A determination can be made that perfusion is absent 210 (e.g., is no longer present) when the current excursion falls below the alert threshold Th, thereby indicating potential cardiac arrest. A personal alarm may be initiated once the alert threshold is broken. If no immediate action to deactivate the personal alarm is detected, an alarm cascade may follow.

In many commercially available photoplethysmographic measuring devices, detecting perfusion 208 may include extracting or otherwise detecting a heartrate from a PPG. Motion artifacts may significantly compromise the physiological signal integrity, thereby greatly encumbering the process by which a heartrate may be detected. A number of embodiments and/or examples described herein may not measure a heart rate, but rather may determine whether perfusion is present 208 as part of detecting cardiac arrest. It is unlikely that a person would be rendered unresponsive by cardiac arrest when perfusion is present 208. This is true regardless of heart rate and enables the method of the present disclosure to function unencumbered by a requirement to determine an exact numerical value for heart rate. Whereas in most electronic signal analyses a prominent signal to noise ratio is important, in the presently disclosed embodiments signal and noise may be processed together or separately. A presence of a signal and noise can indicate a lack of an emergency condition or a lack of cardiac arrest.

Figure 3:
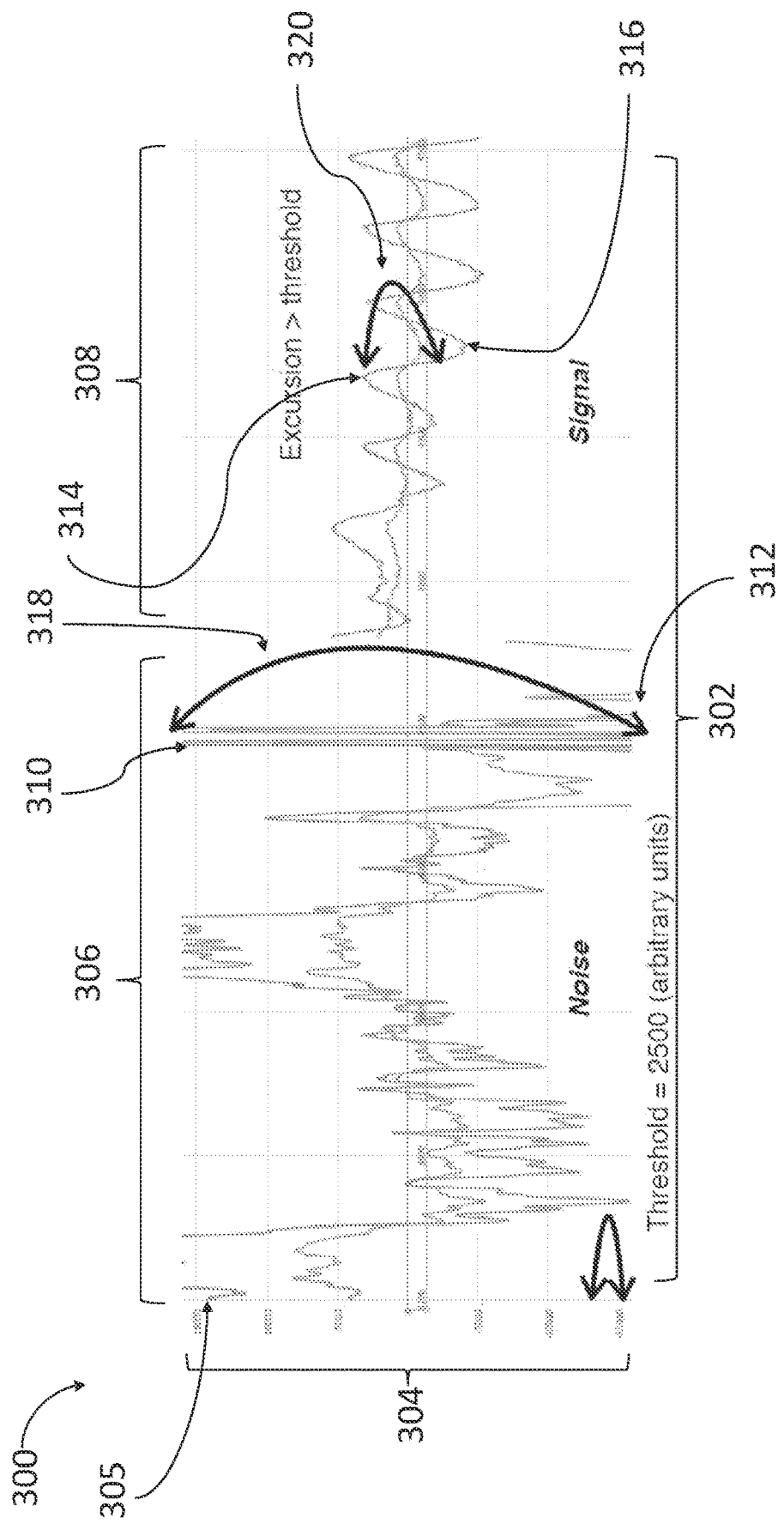
FIG. 3 is a graph illustrating an example of a photoplethysmogram that includes a motion artifact as captured by a photoplethysmographic measuring device, according to one embodiment.

FIG. 3 is a graph 300 illustrating an example of a PPG 305 that includes a motion artifact as captured by a photoplethysmographic measuring device, such as the photoplethysmographic measuring device 140 of FIG. 1, according to one embodiment. In FIG. 3, the PPG 305 may indicate a case where perfusion is present and the photoplethysmographic measuring device is subject to temporary acceleration. The graph 300 of FIG. 3 illustrates the PPG 305 transitioning from a moment where a motion artifact is present 306 to a moment where little to no motion artifact is present 308. FIG. 3 demonstrates that a motion artifact does not hinder the effectiveness of the embodiments of the present disclosure in detecting whether cardiac arrest is present.

In the graph 300 of FIG. 3, the horizontal axis 302 represents units of time and the vertical axis 304 represents a signal level (e.g., an arbitrary unit). The graph 300 illustrates the values that the PPG 305 may take on when a motion artifact is present 306 or is not present 308.

If perfusion is present and a motion artifact is not present 308, the PPG 305 may reach a local maximum value 314 during cardiac systole. If perfusion is present and a motion artifact is not present 308, the PPG 305 may also reach a local minimum value 316 during cardiac diastole.

A motion artifact may be the variations of the PPG 305 that arise from influences other than changes in blood volume within the user's targeted blood vessel(s). Particularly, a motion artifact may be the variations of the PPG 305 that are caused by motion. For example, if the user undergoes any movement, the electromagnetic signal from the photoplethysmographic measuring device (e.g., the electromagnetic signal 112 from the photoplethysmographic measuring device 140 of FIG. 1) may change the direction of the electromagnetic signal and reflect off a part of the user's skin that has different absorption and/or reflection characteristics. In this example, the amount of reflection may vary and may thereby introduce variations in the PPG 305. Another example of a motion artifact is if the user moves such that the source of the electromagnetic signal from the photoplethysmographic measuring device changes its distance from the user's skin, thereby changing the relative intensity of the reflected input signal. In this example, the change in relative intensity of the reflected input signal causes a corresponding variation in the PPG 305. The variations in the PPG 305, due to a motion artifact, may be much larger than those caused by changes in blood volume within the user's targeted blood vessel(s).

When a motion artifact is present 306, the variations of the PPG 305 may be the sum of the variations caused by motion artifacts and the variations caused by perfusion. When the variations caused by motion artifacts and the variations caused by perfusion are summed, the PPG 305 may reach a local maximum value 310 that may or may not occur during cardiac systole. When the variations caused by motion artifact and the variations caused by perfusion are summed, the PPG 305 may also reach a local minimum value 312 that may or may not occur during cardiac diastole.

The variations of the PPG 305 that are caused by motion artifacts may be difficult to predict or analyze. Consequently, obtaining a periodic pattern from the PPG 305 when motion artifacts are present 306 may be difficult or prone to error. However, determining a periodic pattern from the PPG 305 is not necessary to determine whether perfusion is present. The method of the present disclosure does not attempt to identify a periodic pattern from the PPG 305, but rather assesses the excursion of the PPG 305 relative to an alert threshold in order to determine whether perfusion is present. Excursion may be calculated using Equation 1, and the alert threshold may be calculated using Equation 2.

When a motion artifact is not present 308, the excursion 320 of the PPG 305 may have a value larger than that set by the alert threshold, and it may be determined that perfusion is present. When a motion artifact is present 306, the excursion 318 of the PPG 305 may take on a value much larger than that of the excursion 320 of the PPG 305 when a motion artifact is not present 308. In the case where a motion artifact is not present 308, the excursion 320 of the PPG 305 takes on a value that is also larger than the alert threshold. Since the alert threshold is not broken when a motion artifact is present 306 in the PPG 305, no false alarms are triggered on account of motion artifact. As sustained motion artifacts may only occur in persons not suffering cardiac arrest, motion artifacts may be considered to indicate an absence of cardiac arrest.

If perfusion is lost while the user is temporarily in motion, the user will promptly lose consciousness and motion will cease. Once motion has ceased, the loss of perfusion may be detected and an alarm cascade may follow. When movement indicative of usual personal activities is detected, photoplethysmographic monitoring may be switched off, conserving power output, and enabling convenient, comfortable long-term use by virtue of a practical battery size and/or a smaller device. One example is the condition whereupon another embedded sensor (e.g., an accelerometer, gyroscope, or the like) indicates a lack of personal motion. In such a case, photoplethysmographic monitoring may be switched on.

Figure 4A:
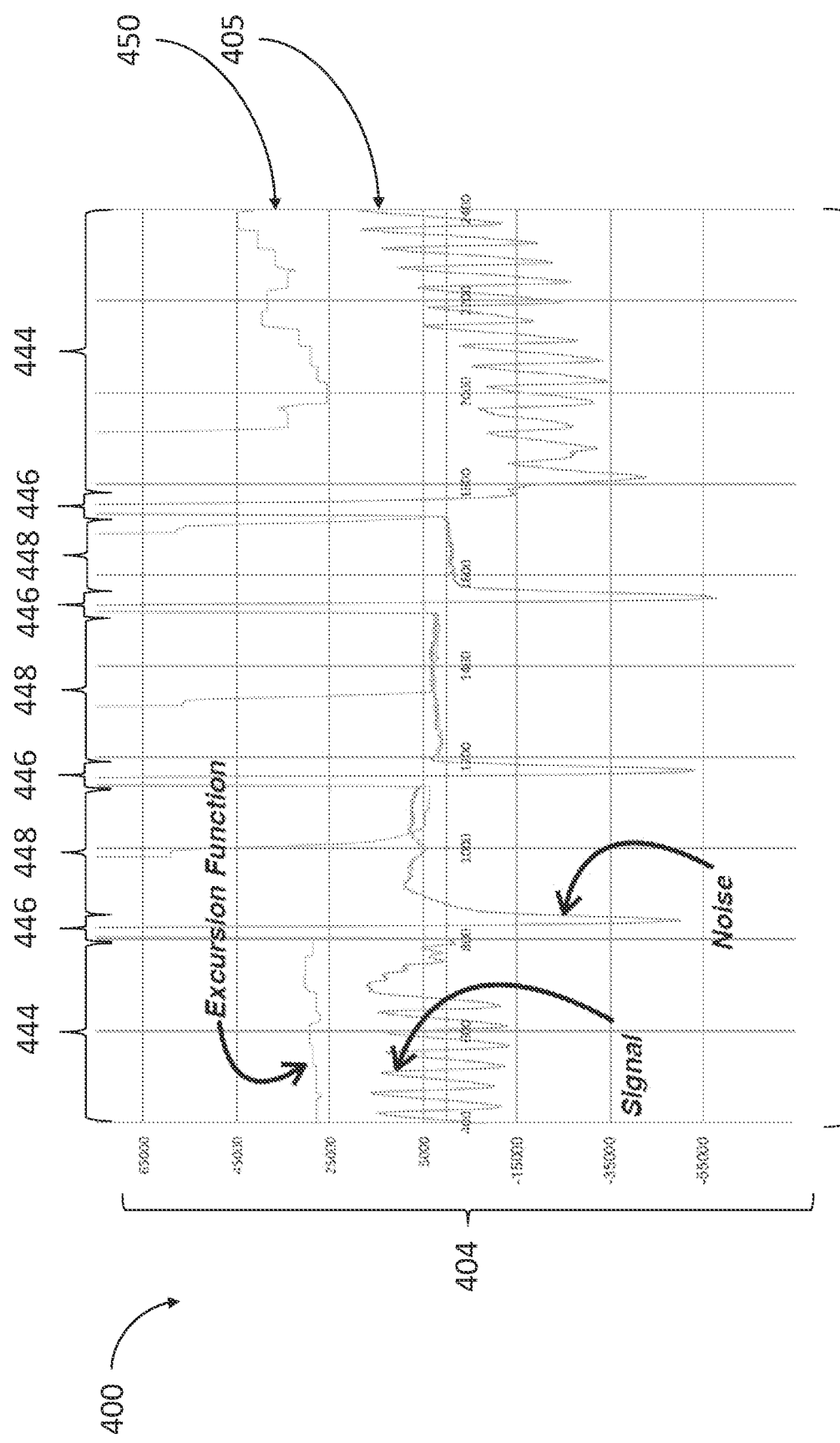
FIG. 4A is a graph illustrating an example of a photoplethysmogram and a graph of an excursion function, according to one embodiment.
Figure 4B:
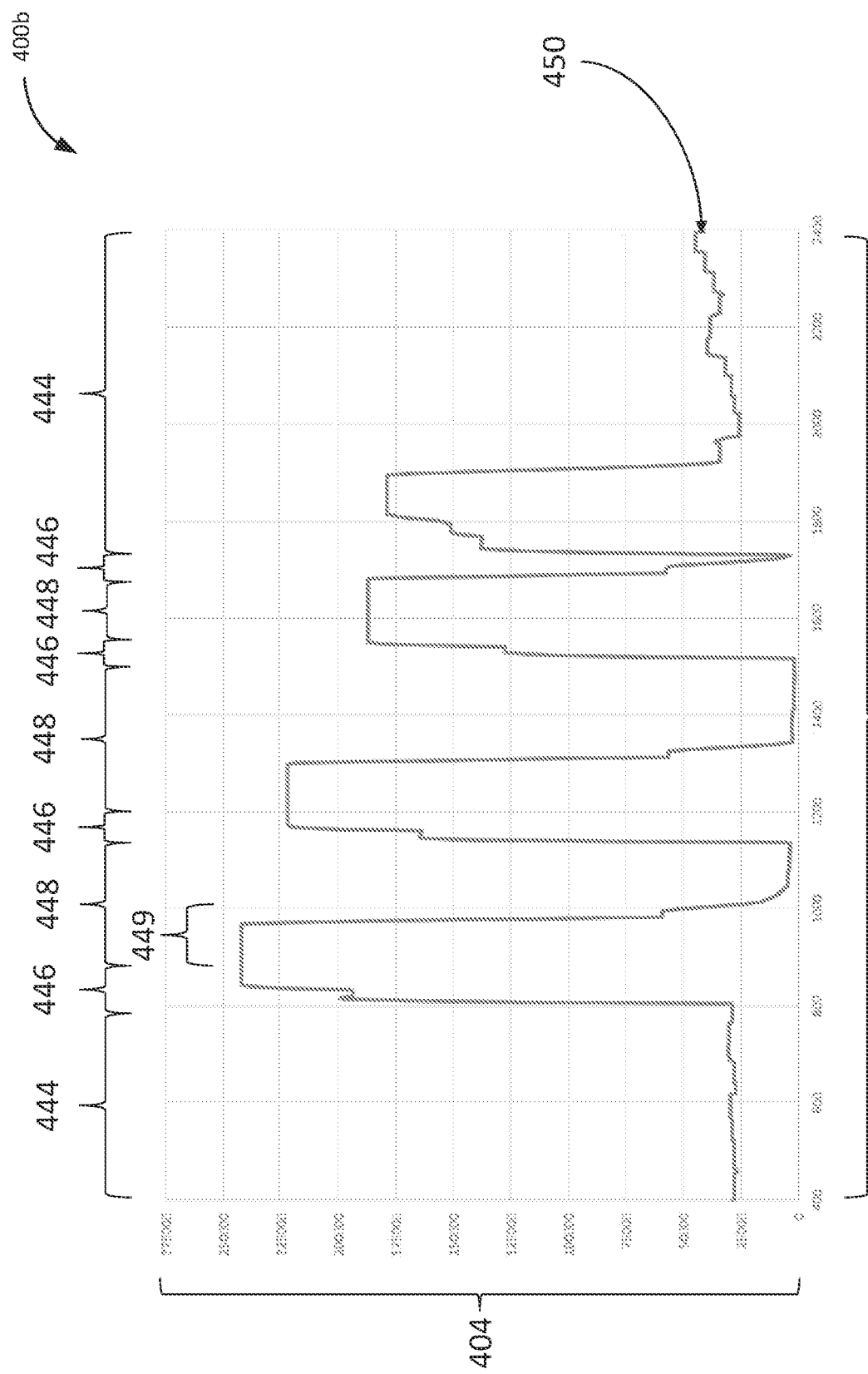
FIG. 4B is a graph illustrating the excursion function of FIG. 4A.
Figure 4C:
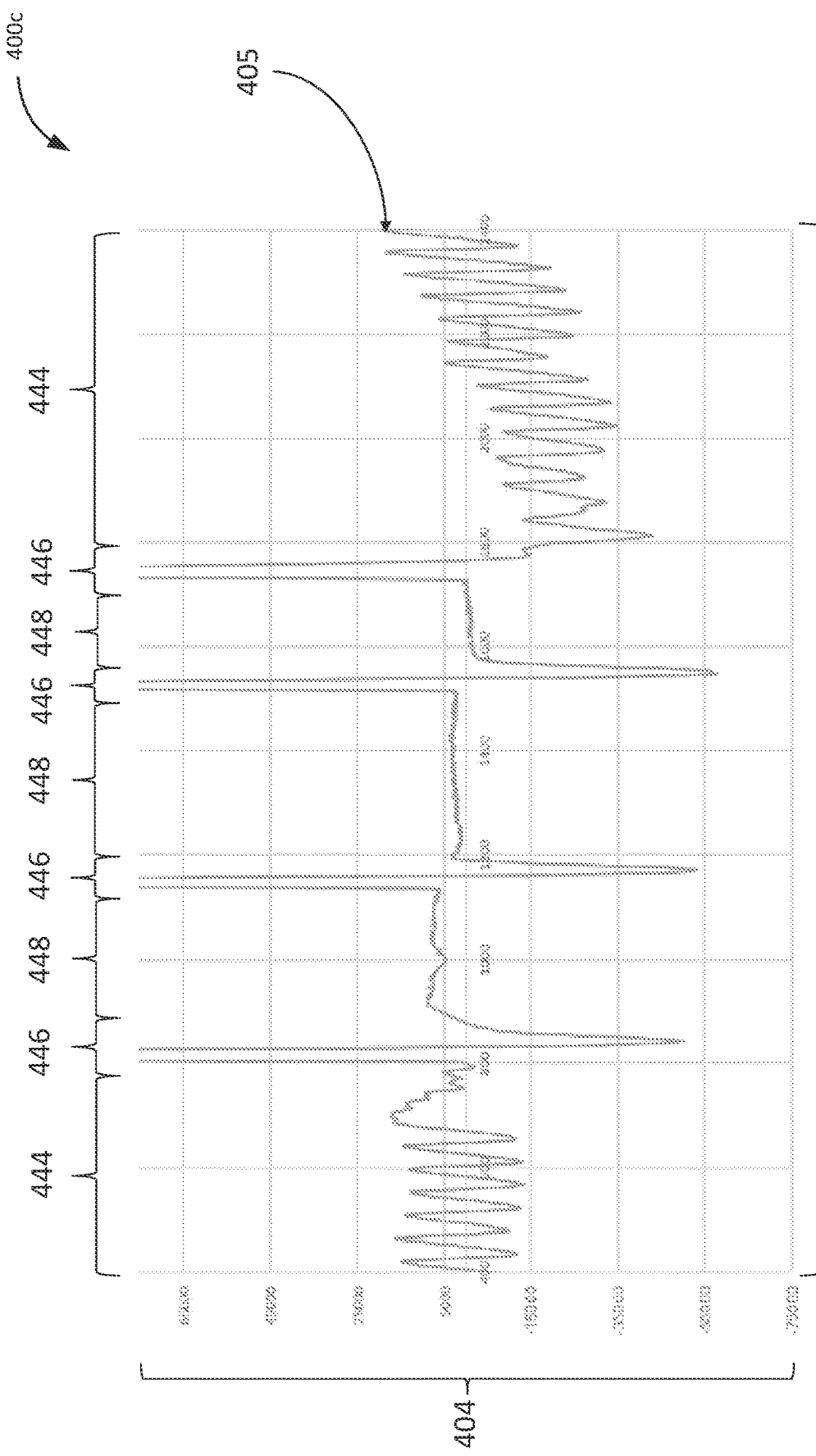
FIG. 4C is a graph illustrating the photoplethysmogram of FIG. 4A.

FIGS. 4A to 4C are graphs 400, 400b, 400c illustrating an example of a PPG 405 and/or an excursion function 450, according to embodiments of the present disclosure. FIG. 4A shows a graph 400 comprising an excursion function 450 and a PPG 405. FIG. 4B shows the graph 400b (e.g., a subset of data of graph 400) comprising the excursion function 450. FIG. 4C shows the graph 400c (e.g., another subset of data of graph 400) comprising the PPG 405.

FIGS. 4A to 4C include a motion artifact 446 as captured by a photoplethysmographic measuring device, such as the photoplethysmographic measuring device 140 of FIG. 1. The PPG 405 and the excursion function 450 include a plurality of instances of perfusion 444, a plurality of instances of motion artifact(s) 446, and a plurality of instances of an absence of both perfusion and motion artifacts 448.

In FIGS. 4A to 4C, the horizontal axis 402 represents units of time and the vertical axis 404 represents a signal level (e.g., an arbitrary unit). The graph 400 illustrates the values that the PPG 405 may take during instances when the motion artifacts are present 446, instances when perfusion is present 444, and instances when there is an absence of both perfusion and motion artifacts 448. The units of time can comprise a duration of time. For example, each unit of time in the horizontal axis 402 can represent one second, two seconds, three seconds, four second, or a different unit of time.

The presence of the motion artifacts 446 is also referenced as noise. The noise can be due to extraneous interference. The excursion function 450 represents a continuous calculation of a difference between a maximum value and minimum value of the PPG 405. The excursion function 450 can lag as compared to the PPG 405. A lag 449 comprises a duration of time in which the maximum value and the minimum value are gathered.

The PPG 405 is recorded from a user experiencing ventricular fibrillation (e.g., cardiac arrest rhythm). During the instances of absence of both perfusion and motion artifacts 448, the values of the excursion function 450 may fall to less than one-fifth of a baseline recording. Cardiac arrest can be identified when, during instances of the absence of both perfusion and motion artifacts 448, the values of the excursion function 450 fall to less than one-fifth of a baseline recording.

Figure 5:
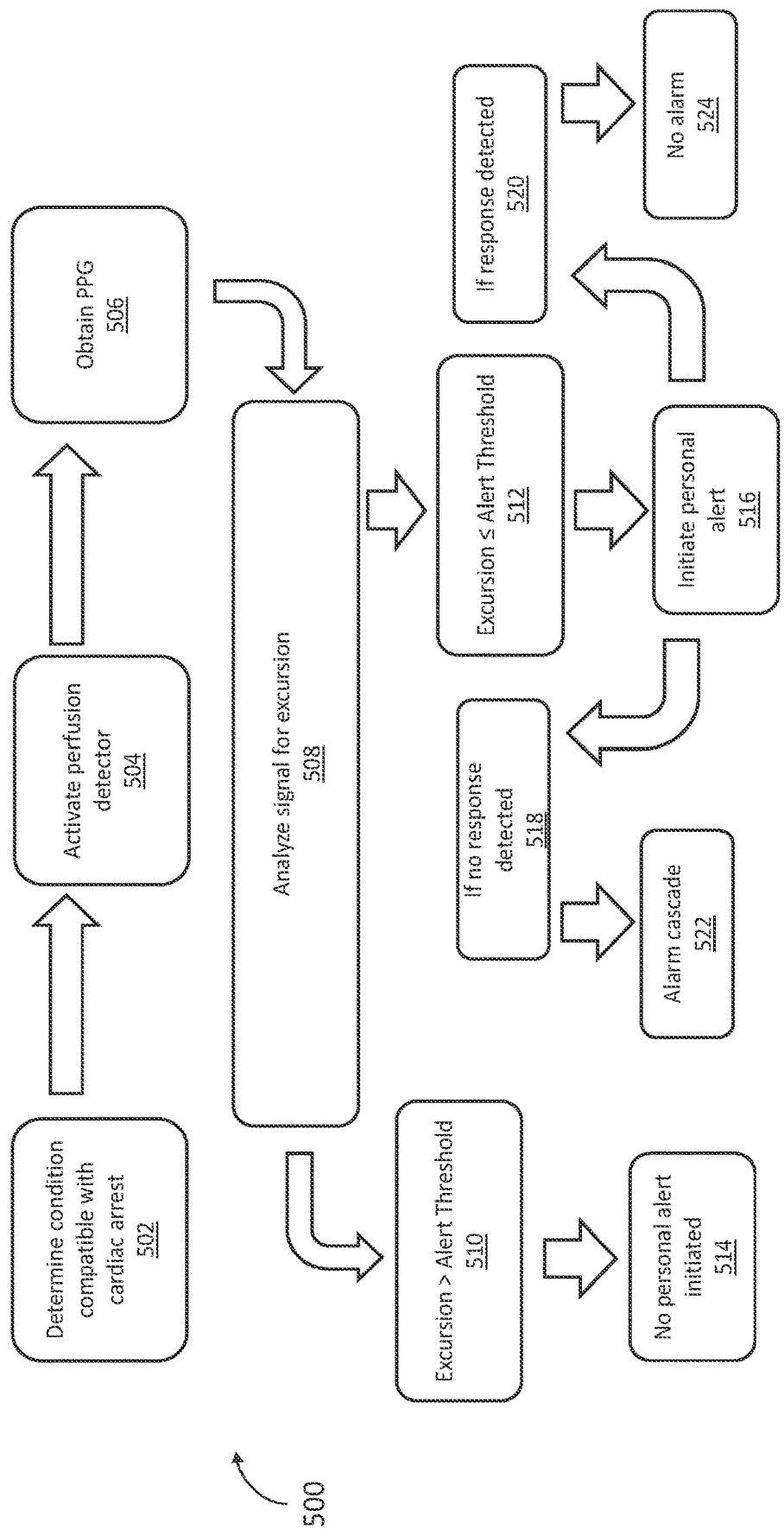
FIG. 5 illustrates a method for detecting cardiac arrest, according to one embodiment.

FIG. 5 illustrates a method 500 for detecting cardiac arrest, according to one embodiment. The method 500 shows operations that may be performed to determine whether perfusion is present in a user, and thereby determine whether the user may be suffering from cardiac arrest. The method 500 may determine whether perfusion is present in the user while conserving power and circumventing false alarms despite the presence of motion artifacts. If a loss of perfusion is detected, a personal alert and possibly an alarm cascade may be initiated.

The method 500 of FIG. 5 may be performed using one or more of an embedded sensor such as an accelerometer, a perfusion detector (e.g., the perfusion detector 100 of FIG. 1), and a variety of external receivers. The embedded sensor (e.g., an accelerometer, a gyroscope, and/or the like) may be used to detect motion, thereby potentially indicating absence of cardiac arrest. If a lack of motion is detected from the embedded sensor, then the perfusion detector may be used to obtain a PPG, and the excursion of the physiological signal shown by the PPG may be analyzed to determine whether perfusion is present. If an absence of perfusion is detected, the variety of external receivers may be used to perform an alarm cascade.

The method 500 may include checking or determining 502 that the user's condition (e.g., state or status) is compatible with cardiac arrest. For example, if it is determined 502 that the user's condition is not compatible with cardiac arrest (e.g., by virtue of motion being detected by an embedded motion sensor), the method 500 may be halted and restarted at a later time, thereby conserving power that would otherwise be consumed by additional operations.

If it is determined 502 that the user's condition is compatible with cardiac arrest at 502, a perfusion detector (e.g., the perfusion detector 100 of FIG. 1) may be activated at 504. The perfusion detector may then obtain 506 a PPG. The physiological signal shown by the PPG may be analyzed 508 for excursion. An excursion value is compared against an alert threshold. For example, it can be determined 510 that the excursion is greater than the alert threshold. It can also be determined 512 that excursion is less than or equal to the alert threshold.

If the excursion value of the physiological signal shown by the PPG is determined 510 to be greater than the alert threshold, then it can be assumed that perfusion is present and the method 500 may be restarted and no personal alert is initiated 514. If the excursion value of the physiological signal shown by the PPG is determined 512 to be less than or equal to the alert threshold, a personal alert may be initiated 516. The user may be given a certain amount of time to respond to the personal alert, and if a response is detected 520, then the method 500 may be restarted and no alarm cascade is initiated at 524. If the user is given a certain amount of time to respond to the personal alert and no response is detected 518, then an alarm cascade may be initiated 522.

As a part of the alarm cascade, previously designated individuals such as a spouse, one or more household members, neighbors, or emergency personnel may be alerted by means of cellular telephones, SMS text, an audible siren, or the like, and the user's location information may be provided within the alert communication. Additionally, network-connected devices such as door locks, and automatic external defibrillators may be activated to facilitate rescue.

Figure 6:
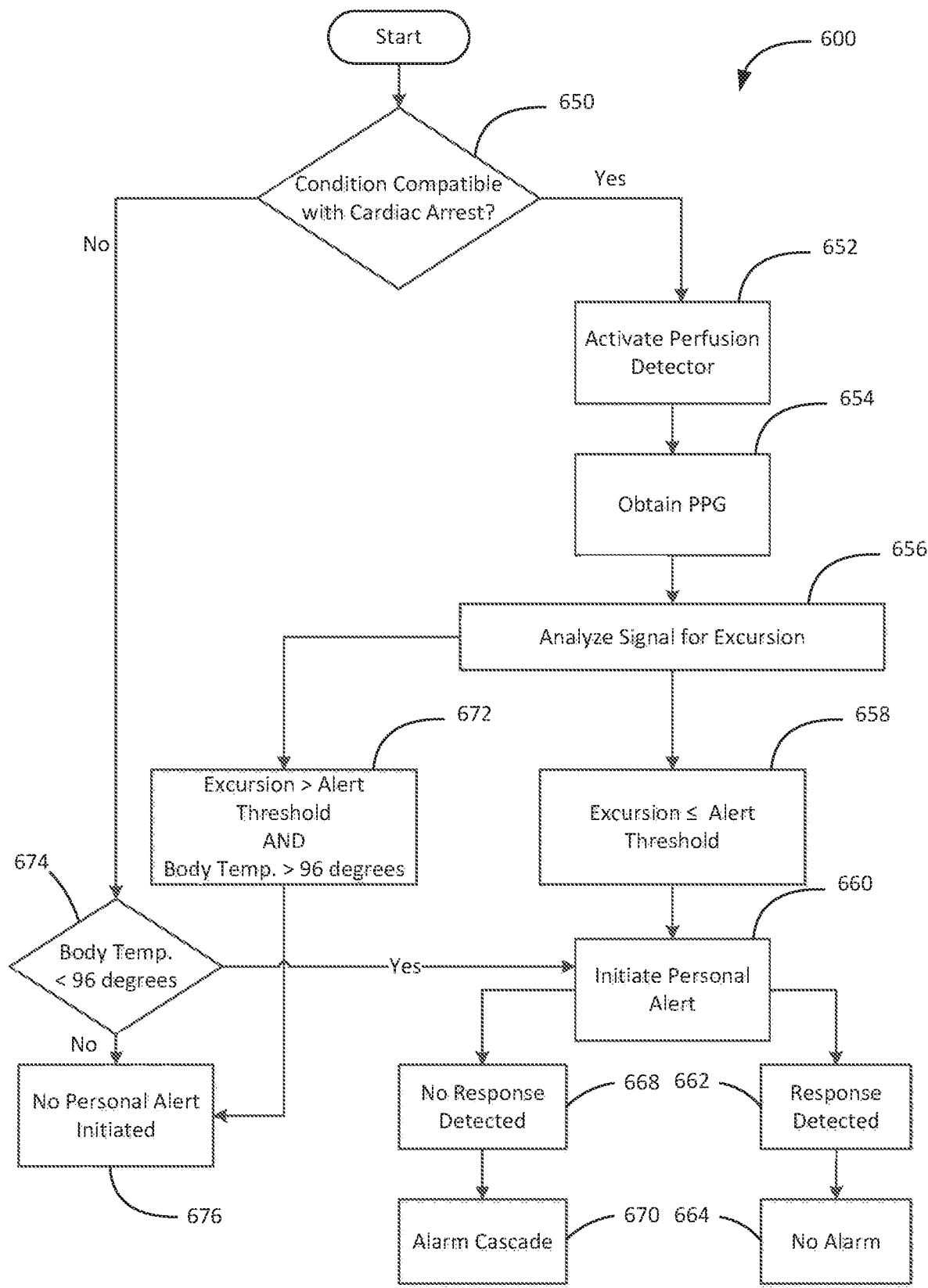
FIG. 6 illustrates a method for detecting cardiac arrest, according to one embodiment.

FIG. 6 illustrates a method 600 for detecting cardiac arrest, according to one embodiment. The method 600 shows operations that may be performed to determine whether perfusion is present in a user, and thereby determine whether the user may be suffering from cardiac arrest. The method 600 may determine whether perfusion is present in the user while conserving power and circumventing false alarms despite the presence of motion artifact(s). If a loss of perfusion is detected, a personal alert and possibly an alarm cascade may be initiated.

The method 600 of FIG. 6 may be performed using one or more of an embedded sensor such as an accelerometer, a perfusion detector (e.g., the perfusion detector 100 of FIG. 1), and a variety of external receivers. The embedded sensor (e.g., an accelerometer, a gyroscope, and/or the like) may be used to detect motion, thereby potentially indicating absence of cardiac arrest. If a lack of motion is detected from the embedded sensor, then the perfusion detector may be used to obtain a PPG, and the excursion of the physiological signal shown by the PPG may be analyzed to determine whether perfusion is present. If an absence of perfusion is detected, the variety of external receivers may be used to perform an alarm cascade.

The method 600 includes determining 650 whether a condition of the user of the perfusion detector is compatible with cardiac arrest. A condition of the user can include a movement of the user, the presence of perfusion, and/or a movement of the perfusion detector in relation to the user, among other conditions of the user that may contribute to a determination of whether the user is experiencing cardiac arrest. For example, the embedded sensor(s) can be used to determine whether a reading of the perfusion detector is due to perfusion or a motion artifact.

The embedded sensor(s) can indicate that the perfusion detector is in motion. The embedded sensor(s) can sense, for example, acceleration to determine motion. The acceleration can indicate that the reading generated by the perfusion detector is attributed to a motion artifact. In some examples, a user may travel in a vehicle, such as an airplane, a bus, and/or a train, among other possible vehicles that can transport users. The embedded sensor(s) can indicate motion. For example, the embedded sensor(s) can report a change in global positioning system (GPS) coordinates. A change in GPS coordinates can be indicative of user movement which may be attributed to travel. Such movement indicates that the condition of the user is not compatible with cardiac arrest.

In response to determining 650 that a condition of the user is not compatible with cardiac arrest, the method 600 determines 674 whether the body temperature of the user is less than 96 degrees. The perfusion detector can include a temperature sensor. The temperature sensor can be, for example, a thermistor sensor. The temperature sensor indicates to the perfusion detector a temperature of the user and/or the perfusion detector. The perfusion detector can determine 674, via the signal processor 150 (see FIG. 1), whether the user's temperature is less than 96 degrees.

A user temperature that is less than 96 degrees is indicative of possible cardiac arrest or other issue. Although 96 degrees is used in the example shown in FIG. 6, other temperature thresholds can be selected. For example, a temperature threshold can be equal to 97 degrees or 95 degrees, among other temperature thresholds. As a user experiences cardiac arrest, the temperature of the user drops.

Determining 674 that the temperature of the user is less than 96 degrees in conjunction with the determination 650 that the user condition is not compatible with cardiac arrest is indicative that a user is experiencing cardiac arrest while the perfusion detector and/or the user is moving. For example, the user can experience cardiac arrest while traveling in a vehicle.

The method 600 can proceed to initiate 660 a personal alert based on a determination 674 that the user temperature is less than 96 degrees. The method 600 can proceed to abstain 676 from initiating a personal alert based on the determination 674 that the user temperature is greater than 96 degrees.

In response to determining 650 that a condition of the user is compatible with cardiac arrest (e.g., no movement detected), the method 600 can proceed to activate 652 the perfusion detector. Based on activating 652 the perfusion detector, the method 600 obtains 654 the PPG. The method 600 then analyzes 656 the signal, obtained by the perfusion detector, to determine whether excursion is present. Based on a determination 672 that excursion (e.g., the signal indicative of excursion) is greater than an alert threshold and that the body temperature is greater than or equal to 96 degrees, the method can proceed to abstain 676 from initiating a personal alert. Although not shown, the method 600 can proceed to initiate 660 a personal alert if excursion is less than or equal to an alert threshold and the body temperature of the user is greater than or equal to 96 degrees.

Based on a determination 658 that excursion is less than or equal to the alert threshold, the method 600 can proceed to initiate 660 a personal alert. In response to initiating 660 the personal alert, the method 600 can determine 668 that no response is detected or determine 662 that a response is detected. The response can include a response by the user. The response can be an interaction with the perfusion detector or a change in the user such that excursion is greater than an alert threshold.

If no response is detected, then an alarm cascade can be initiated 670 to take further action to illicit a response from the user. If a response is detected, the method 600 abstains 664 from initiating an alarm cascade.

The disclosed systems and apparatuses may include one or more processors to execute operations to detect cardiac arrest. For example, the signal processor 150 of FIG. 1 may comprise one or more processors. The one or more processors may include one or more general purpose devices, such as an Intel®, AMD®, or other standard microprocessor and/or microcontroller. The one or more processors may include a special purpose processing device, such as an ASIC, SoC, SiP, FPGA, PAL, PLA, FPLA, PLD, or other customized or programmable device. The one or more processors may perform distributed (e.g., parallel) processing to execute or otherwise implement functionalities of the present embodiments. The one or more processors may run a standard operating system and perform standard operating system functions. It is recognized that any standard operating system may be used, such as, for example, Microsoft® Windows®, Apple® MacOS®, Disk Operating System (DOS), UNIX, IRJX, Solaris, SunOS, FreeBSD, Linux®, or ffiM® OS/2® operating system, and so forth. In some examples, the one or more processors may run application software to execute operations to detect cardiac arrest without the use of an operating system. For example, the application software may run bare metal on the one or more processors.

The one or more processors may be in electronic communication with an electronic memory, which may include static RAM, dynamic RAM, flash memory, one or more flip-flops, ROM, CD-ROM, DVD, disk, tape, or magnetic, optical, or other computer storage medium. The electronic memory may include a plurality of program modules and program data.

The program modules may include all or portions of other elements of the system. The program modules may run multiple operations concurrently or in parallel by or on the one or more processors. In some embodiments, portions of the disclosed modules, components, and/or facilities are embodied as executable instructions embodied in hardware or in firmware, or stored on a non-transitory, machine-readable storage medium. The instructions may comprise computer program code that, when executed by a processor and/or computing device, cause a computing system to implement certain processing steps, procedures, and/or operations, as disclosed herein. The modules, components, and/or facilities disclosed herein may be implemented and/or embodied as a driver, a library, an interface, an API, FPGA configuration data, firmware (e.g., stored on an EEPROM), and/or the like. In some embodiments, portions of the modules, components, and/or facilities disclosed herein are embodied as machine components, such as general and/or application-specific devices, including, but not limited to: circuits, integrated circuits, processing components, interface components, hardware controller(s), storage controller(s), programmable hardware, FPGAs, ASICs, and/or the like.

The program data stored on the electronic memory may include data generated by the system, such as by the program modules or other modules. The stored program data may be organized as one or more databases.

A perfusion detector may include an I/O interface, which may facilitate interfacing with one or more input devices and/or one or more output devices. The input device(s) may include a keyboard, mouse, touch screen, light pen, tablet, microphone, sensor, or other hardware with accompanying firmware and/or software. The output device(s) may include a monitor or other display, printer, speech or text synthesizer, switch, signal line, or other hardware with accompanying firmware and/or software. In some examples, output device(s) may also include wireless output devices such as WiFi devices, Bluetooth devices, and/or other wireless technologies. The wireless output device may be used to facilitate communications via a cell phone, for example. The output devices may also be wired output devices such as universal serial bus (USB) devices.

As can be appreciated, other methods and processes are available and included in the descriptions above describing operation of the system embodiments and are within the scope of the present disclosure.

EXAMPLE EMBODIMENTS

Some examples of embodiments of systems and methods of anonymized transparent exchange of information are provided below.

Example 1. An apparatus for detecting cardiac arrest, comprising a photoplethysmographic measuring device, including a transmitter module to transmit a signal toward a user to interact with the skin of the user and a receiver module to receive a reflection of the signal and generate a photoplethysmogram; and a signal processor to process the photoplethysmogram to detect whether the user is experiencing cardiac arrest.

Example 2. The apparatus of Example 1, wherein the signal processor to process the photoplethysmogram is further configured to detect perfusion in the user to determine whether the user is experiencing cardiac arrest.

Example 3. The apparatus of Example 1, further comprising an alarm mechanism to alert others that the user is experiencing cardiac arrest based on a determination that the user is experiencing cardiac arrest.

Example 4. The apparatus of Example 1, further comprising a personal alarm to, upon detection of cardiac arrest in the user, attempt to arouse a response in the user.

Example 5. The apparatus of Example 1, further comprising a sensor to detect whether a condition of the user is compatible with cardiac arrest.

Example 6. The apparatus of Example 5, wherein the sensor comprises one or more of a gyroscope and an accelerometer to detect movement of the user.

Example 7. The apparatus of Example 1, wherein the signal transmitted toward the user to interact with the skin comprises an electromagnetic signal.

Example 8. The apparatus of claim 7, wherein the electromagnetic signal comprises green visible light.

Example 9. A perfusion detector for detecting cardiac arrest, comprising a photoplethysmographic measuring device, including: a transmitter module to transmit a signal toward a user to interact with the skin of the user, and a receiver module to receive a reflection of the signal; a signal processor to: process a photoplethysmogram obtained by the photoplethysmographic measuring device to detect whether perfusion is present in the user, wherein the photoplethysmogram is generated from the reflection of the signal; and determine whether the user is experiencing cardiac arrest based on whether perfusion is present in the user; and an alarm mechanism to alert others that the user is experiencing cardiac arrest based on a determination that the user is experiencing cardiac arrest.

Example 10. The perfusion detector of Example 9, further comprising a personal alarm to evoke a response in the user, upon detection of cardiac arrest in the user.

Example 11. The perfusion detector of Example 9, wherein the receiver module comprises one or more individual transducers to receive the reflection of the signal.

Example 12. The perfusion detector of Example 11, wherein the photoplethysmographic measuring device is further configured to measure a resolution of the reflection of the signal.

Example 13. The perfusion detector of Example 12, wherein the photoplethysmographic measuring device is further configured to: determine whether the resolution of the reflection of the signal is less than or equal to a threshold; and based on a determination that the resolution is less than or equal to the threshold, activate an additional number of individual transducers to receive the reflection of the signal to increase the resolution of the signal.

Example 14. A method for monitoring for cardiac arrest in an individual, the method comprising: transmitting a signal toward a user to interact with the skin of the user; receiving a reflection of the signal; generating a photoplethysmogram based on the reflected signal; determining from the photoplethysmogram whether perfusion is present in the skin of the user; and determining, based on a presence of perfusion, whether the user is experiencing cardiac arrest.

Example 15. The method of Example 14, wherein receiving the reflection of the signal further comprises receiving the reflection of the signal through one or more individual transducers.

Example 16. The method of Example 15, further comprising deactivating a portion of the one or more individual transducers to decrease power consumption.

Example 17. A computer readable storage medium having stored thereon instructions that, when implemented by a computing device, cause the computing device to activate a perfusion detector based on sensor input received from a sensor; transmit, via the perfusion detector, a signal toward a user to interact with the skin of the user; receive, via the perfusion detector, a reflection of the signal; generate a photoplethysmogram based on the reflection of the signal; process the photoplethysmogram to detect perfusion in the user; determine whether the user is experiencing cardiac arrest based on a detected perfusion in the user; and initiate an alarm if the user is experiencing cardiac arrest.

Example 18. The computer readable storage medium of Example 17, wherein the sensor captures personal motion, wherein the sensor input provides an indication whether personal motion is occurring as captured by the sensor.

Example 19. The computer readable storage medium of Example 18, wherein the instructions are further configured to activate the perfusion detector based on a determination that the sensor input does not indicate personal motion is occurring.

Example 20. The computer readable storage medium of Example 17, wherein the instructions to process the photoplethysmogram to detect perfusion further comprises instructions to detect perfusion without regard to motion artifacts.

Example 21 is a photoplethysmographic measuring device for detecting cardiac arrest. The photoplethysmographic measuring device includes electronic memory to store a photoplethysmogram. The photoplethysmographic measuring device also includes one or more processors designed to transmit a signal toward a user to interact with the skin of the user, receive a reflection of the signal, generate the photoplethysmogram based on the reflection of the signal, and process the photoplethysmogram to detect whether the user is experiencing cardiac arrest.

Example 22 is the photoplethysmographic measuring device of Example 21, where the one or more processors are further designed to process the photoplethysmogram to detect perfusion in the user to determine whether the user is experiencing cardiac arrest.

Example 23 is the photoplethysmographic measuring device of Example 21, also including an alarm mechanism to alert others that the user is experiencing cardiac arrest based on a determination that the user is experiencing cardiac arrest.

Example 24 is the photoplethysmographic measuring device of Example 21, also including a personal alarm designed to, upon detection of cardiac arrest in the user, arouse a response in the user.

Example 25 is the photoplethysmographic measuring device of Example 21, also including a sensor to detect whether a condition of the user is compatible with cardiac arrest.

Example 26 is the photoplethysmographic measuring device of Example 21, where the sensor includes one or more of a gyroscope and an accelerometer to detect movement of the user.

Example 27 is the photoplethysmographic measuring device of Example 21, where the signal transmitted toward the user to interact with the skin includes an electromagnetic signal.

Example 28 is the photoplethysmographic measuring device of Example 27, where the electromagnetic signal includes green visible light.

Example 29 is an apparatus for detecting cardiac arrest. The apparatus includes electronic memory to store a photoplethysmogram. The apparatus also includes one or more processors configured to transmit a signal toward a user to interact with the skin of the user, receive a reflection of the signal, generate a photoplethysmogram from the reflection of the signal, process the photoplethysmogram to detect whether perfusion is present in the user and determine whether the user is experiencing cardiac arrest; and an alarm mechanism to alert others that the user is experiencing cardiac arrest.

Example 30 is the apparatus of Example 29, further including a personal alarm to attempt to evoke a response in the user, upon detection of cardiac arrest in the user.

Example 31 is a method for monitoring for cardiac arrest in an individual. The method includes transmitting a signal toward a user to interact with the skin of the user, receiving a reflection of the signal, generating a photoplethysmogram based on the reflection of the signal, determining from the photoplethysmogram whether perfusion is present in the skin of the user, and determining based on the presence of perfusion whether the user is experiencing cardiac arrest.

Example 32 is a computer-readable storage medium having stored thereon instructions that, when implemented by an apparatus for detecting cardiac arrest, cause the apparatus to transmit, via a transmitter module, a signal toward a user to interact with the skin of the user; receive, via a receiver module, a reflection of the signal; generate, via the receiver module, a photoplethysmogram; process, via a signal processor, the photoplethysmogram to detect perfusion in the user; receive, via a processing module, sensor input from a sensor to determine whether a condition of the user is compatible with cardiac arrest and activate a perfusion detector if the condition is compatible with cardiac arrest; receive, via the processing module, perfusion input from the signal processor indicating perfusion in the user; determine, via the processing module, based on the sensor input and the perfusion input whether the user is experiencing cardiac arrest; and initiate, via the processing module, an alarm if the user is experiencing cardiac arrest to notify rescuers of the cardiac arrest.

The foregoing specification has been described with reference to various embodiments. However, those skilled in the art appreciate that various modifications and changes can be made without departing from the scope of the present disclosure and the underlying principles of the invention. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element.

While the principles of this disclosure have been shown in various embodiments, many modifications of structure, arrangements, proportions, the elements, materials and components, used in practice, which are particularly adapted for a specific environment and operating requirements, may be used without departing from the principles and scope of this disclosure. These and other changes or modifications are intended to be included within the scope of the present disclosure. Those having skill in the art will recognize that many changes may be made to the details of the above-described embodiments without departing from the underlying principles of the invention. The scope of the present invention should, therefore, be determined only by the following claims.

The invention claimed is:

1. An apparatus for detecting cardiac arrest, comprising:
 a photoplethysmographic measuring device including:
  a transmitter to provide a transmission of a signal to interact with tissue of a user, and
  a receiver module to:
   receive the transmission of the signal; and
   generate a photoplethysmogram; and
 a signal processor to process the photoplethysmogram to detect perfusion in the tissue of the user to determine whether the user is experiencing cardiac arrest, wherein the signal processor detects perfusion in the user by calculating an excursion value based on a maximum value and a minimum value of the photoplethysmogram during a time period.

2. The apparatus of claim 1, further comprising an alarm mechanism to alert others that the user is experiencing cardiac arrest based on a determination that the user is experiencing cardiac arrest.

3. The apparatus of claim 1, further comprising a personal alarm to, upon detection of cardiac arrest in the user, attempt to arouse a response in the user.

4. The apparatus of claim 1, further comprising a sensor to detect whether a condition of the user is compatible with cardiac arrest.

5. The apparatus of claim 4, wherein the sensor comprises one or more of a gyroscope and an accelerometer to detect movement of the user.

6. The apparatus of claim 1, wherein the transmission of the signal toward the user to interact with the tissue comprises a transmission of an electromagnetic signal.

7. The apparatus of claim 1, wherein the transmission of the signal toward the user to interact with the tissue comprises a transmission of light.

8. The apparatus of claim 1, wherein the receiver module is positioned to receive the transmission of the signal as reflected from the tissue of the user.

9. The apparatus of claim 1, wherein the receiver module is positioned to receive the transmission of the signal as transmitted through the tissue of the user.

10. The apparatus of claim 1, wherein the tissue of the user comprises skin of the user.

11. The apparatus of claim 1, wherein the transmission of the signal interacts with blood cells in the tissue of the user.

12. A perfusion detector for detecting cardiac arrest, comprising:
   a photoplethysmographic measuring device including:
      a transmitter module to transmit a signal toward tissue of a user, and
      a receiver module to receive a transmission of the signal;
   a signal processor to:
      process a photoplethysmogram obtained by the photoplethysmographic measuring device to detect whether perfusion is present in the user, wherein the photoplethysmogram is generated from the transmission of the signal; and
      determine whether the user is experiencing cardiac arrest based on whether perfusion is present in the user,
      wherein the signal processor detects perfusion in the user by calculating an excursion value based on a maximum value and a minimum value of the photoplethysmogram during a time period; and
   an alarm mechanism to alert that the user is experiencing cardiac arrest based on a determination that the user is experiencing cardiac arrest.

13. The perfusion detector of claim 12, further comprising a personal alarm to evoke a response in the user, upon detection of cardiac arrest in the user.

14. The perfusion detector of claim 12, wherein the receiver module comprises one or more individual transducers positioned to receive the transmission of the signal as a reflection of the signal off the tissue of the user.

15. The perfusion detector of claim 12, wherein the receiver module comprises one or more individual transducers positioned to receive the transmission of the signal through the tissue of the user.

16. The perfusion detector of claim 12, wherein the photoplethysmographic measuring device is further configured to measure a resolution of the transmission of the signal.

17. The perfusion detector of claim 16, wherein the photoplethysmographic measuring device is further configured to:
   determine whether the resolution of the transmission of the signal is less than or equal to a threshold; and
   based on a determination that the resolution is less than or equal to the threshold, activate an additional number of individual transducers to receive the transmission of the signal to increase the resolution of the transmission of the signal.

18. The perfusion detector of claim 12, wherein the tissue of the user comprises skin of the user.

19. The perfusion detector of claim 12, wherein the transmission of the signal interacts with blood cells in the tissue of the user.

20. The perfusion detector of claim 12, wherein the transmission of the signal toward the user to interact with the tissue comprises a transmission of light.

* * * * *